US010455833B2

(12) United States Patent
Holden

(10) Patent No.: US 10,455,833 B2
(45) Date of Patent: Oct. 29, 2019

(54) METHODS OF RAPIDLY PREVENTING THE SPREAD OF AVIAN INFLUENZA VIRUS IN POULTRY FLOCKS

(71) Applicant: AGRO INNOVATION INTERNATIONAL (A.I.I.), Saint Malo (FI)

(72) Inventor: Cody J. Holden, Pine Grove, PA (US)

(73) Assignee: AGRO INNOVATION INTERNATIONAL (A.I.I.), Saint Malo (FR)

(*) Notice: Subject to any disclaimer, the term of this patent is extended or adjusted under 35 U.S.C. 154(b) by 0 days.

(21) Appl. No.: 15/792,280

(22) Filed: Oct. 24, 2017

(65) Prior Publication Data

US 2018/0110221 A1 Apr. 26, 2018

Related U.S. Application Data

(60) Provisional application No. 62/510,709, filed on May 24, 2017, provisional application No. 62/412,159, filed on Oct. 24, 2016.

(51) Int. Cl.

| *A01N 37/40* | (2006.01) |
|---|---|
| *A01N 59/06* | (2006.01) |
| *A01N 25/12* | (2006.01) |
| *A01N 25/34* | (2006.01) |
| *A01N 37/10* | (2006.01) |
| *A01N 59/08* | (2006.01) |
| *A01N 59/20* | (2006.01) |
| *A61K 31/60* | (2006.01) |

(52) U.S. Cl.
CPC ............ *A01N 37/40* (2013.01); *A01N 25/12* (2013.01); *A01N 25/34* (2013.01); *A01N 37/10* (2013.01); *A01N 59/06* (2013.01); *A01N 59/08* (2013.01); *A01N 59/20* (2013.01); *A61K 31/60* (2013.01)

(58) Field of Classification Search
None
See application file for complete search history.

(56) References Cited

U.S. PATENT DOCUMENTS

| 6,294,186 B1 * | 9/2001 | Beerse | A01N 43/36 424/401 |
|---|---|---|---|
| 8,034,844 B2 * | 10/2011 | Fox | A01N 31/02 424/78.37 |
| 2006/0247161 A1 | 11/2006 | Planz et al. | |
| 2012/0288488 A1 | 11/2012 | Sookram et al. | |

FOREIGN PATENT DOCUMENTS

| CN | 104784199 A | 7/2015 |
|---|---|---|
| CN | 105232763 A | 1/2016 |
| EP | 2289520 A1 | 3/2011 |
| WO | WO-0128338 A2 | 4/2001 |
| WO | WO-2018078532 A1 | 5/2018 |

OTHER PUBLICATIONS

Jacob et al (Animal Sciences Department, UF/IFAS Extension, Document PS38:1-3, 1998) (Year: 1998).*
Baert, K. and De Backer, P., "Disposition of Sodium Salicylate, Flunixin and Meloxicam after Intravenous Administration in Broiler Chickens," Journal of Veterinary Pharmacology and Therapeutics 25(6):449-453, Blackwell Scientific Publications, England (Dec. 2002).
Easterday, B. C. et al., "Influenza" in Diseases of Poultry, 10 ed., Calnek, B.W. et al. (eds.), Iowa State University Press, United States, pp. 583-605 (1997).
Capua, I. and Alexander, D.J., "Avian Influenza: Recent Developments," Avian Pathology 33(4):393-404, Informa Healthcare, England (Aug. 2004).
Capua, I. and Marangon, S., "Control of Avian Influenza in Poultry," Emerging Infectious Diseases 12(9):1319-1324, National Center for Infectious Diseases, United States (Sep. 2006).
Dinh, P.N., et al., "Risk Factors for Human Infection with Avian Influenza a H5N1, Vietnam, 2004," Emerging Infectious Diseases 12(12):1841-1847, National Center for Infectious Diseases, United States (Dec. 2006).
Escorcia, M., et al., "Avian Influenza: Genetic Evolution under Vaccination Pressure," Virology Journal 5:15, BioMed Central, England (Jan. 2008).
Gatherer, D., et al., "The 2009 H1N1 Influenza Outbreak in its Historical Context," Journal of Clinical Virology 45(3):174-178, Elsevier Science, Netherlands (Jul. 2009).
International Search Report and Written Opinion for International Application No. PCT/IB2017/056603, European Patent Office, Rijswijk, dated Mar. 19, 2018, 11 pages.
Oie, "Avian Influenza," in Manual of Diagnostic Tests and Vaccines for Terrestrial Animals, 15th ed, France, pp. 302-309 (2006).
Oie, "Avian Influenza," in Terrestrial Animal Health Code, vol. 2, Chapter 10.4, France, pp. 526-543 (2011).
Oie, "Infection with Avian Influenza Viruses," in Terrestrial Animal Health Code, vol. 2, Chapter 10.4, pp. 556-572 (2017).
Sell, C., "The Chemistry of Essential Oils," in Handbook of Essential Oils Science, Technology, and Applications, Can Baser, K.H. and Buchbauer, G., eds., pp. 121-150, CRC Press, Boca Raton, FL (2010).
Swayne, D.E. and Halvorson, D.A., "Chapter 6:Influenza," pp. 153-184, in Diseases of Poultry, 11$^{th}$ edition, Saif, Y.M. et al., ed., Iowa State Press (2008).

(Continued)

*Primary Examiner* — Craig D Ricci
(74) *Attorney, Agent, or Firm* — Sterne, Kessler, Goldstein & Fox P.L.L.C.

(57) ABSTRACT

Methods for rapidly preventing, controlling, or stopping the spread of Avian Influenza Virus (AIV) in the housing of a poultry flock in need thereof are provided, comprising, applying a composition to the floor of said housing in amounts effective to rapidly inactivate AIV, said composition comprising (i) salicylic acid; and (ii) one or more mineral salts, wherein said inactivation occurs within about ten to fifteen minutes after application of said composition, thereby preventing, controlling, or stopping the spread of AIV in said housing.

19 Claims, No Drawings

(56) References Cited

OTHER PUBLICATIONS

Thayer, S.G. and Beard, C.W., "Chapter 47—Serologic Procedures," pp. 222-229, in A Laboratory Manual for the Isolation and Identification of Avian Pathogens, Swayne, D.E. et al., eds., International Book Distributing Co., India (2008).
U.S. Animal Health Association, Report of the Committee of Transmissible Disease of Poultry and Other Avian Species, Proceedings of the United States Animal Health Association: pp. 490-533, United States (1994).
Vong, S., et al., "Risk Factors Associated with Subclinical Human Infection with Avian Influenza a (H5N1) Virus—Cambodia, 2006," The Journal of Infectious Diseases 199(12):1744-1752, Oxford University Press, United States (Jun. 2009).
Wang, M., et al., "Food Markets with Live Birds as Source of Avian Influenza," Emerging Infectious Diseases 12(11):1773-1775, National Center for Infectious Diseases, United States (Nov. 2006).
Safety Data Sheet for "Shield Plus," Timac AGRO, Sep. 2, 2016, 7 pages.
Grassland AGRO brochure, "Actisan—Bedding Disinfectant for Animal Housing," Ireland, 2010, 2 pages.
Galloway & Macleod brochure, "Actisan New Generation Anti-Bacterial Bedding Conditioner," NUTRIFERTIL, United Kingdom, 2010, 2 pages.
Lu, H., et al., "Shield Plus, A Natural Animal Welfare Enhancer and Disinfectant for Inactivation Studies on Avian Influenza and Other Avian Viruses," Poster Presentation for AVMA-AAAP (American Association of Avian Pathologists), Jul. 13-Jul. 17, 2018, Denver, Colorado (United States).
Lu, H.. et al., "Survival of Avian Influenza Virus H7N2 in SPF Chickens and Their Environments," *Avian Diseases* 47:1015-1021, The American Association of Avian Pathologists, United. States (2003).
Pearson, J.E., et al., "Diagnostic Procedures for Avian Influenza," Proceedings of the Second International Symposium on Avian Influenza, pp. 222-227, (Georgia Center for Continuing Education), Sep. 3-5, 1986, Athens, Georgia (United States).
Spackman, E. and Killian M.L., "Chapter 12:Avian Influenza Virus Isolation, Propagation, and Titration in Embryonated Chicken Eggs," in *Animal Influenza Virus*, Spackman, E., ed., $2^{nd}$ ed., Methods of Molecular Biology, vol. 1161, pp. 125-140, Springer Science+Business Media, United States (2014).
Swayne, D.E., et al., "Chapter 29:Avian Influenza," pp. 150-155, in *A Laboratory Manual for the Isolation and Identification of Avian Pathogens*, Swayne, D.E. et al., eds., $4^{th}$ed., American Association of Avian Pathologists, Inc., United States (1998).

* cited by examiner

METHODS OF RAPIDLY PREVENTING THE SPREAD OF AVIAN INFLUENZA VIRUS IN POULTRY FLOCKS

CROSS REFERENCE TO RELATED APPLICATIONS

Related applications U.S. Provisional Appl. No. 62/510,709, filed May 24, 2017, and U.S. Provisional Appl. No. 62/412,159, filed Oct. 24, 2016, are herein incorporated by reference in their entireties.

BACKGROUND OF THE INVENTION

Field of the Invention

The present invention relates generally to the fields of avian virology and agricultural biosecurity. More particularly, the present invention relates to methods of rapidly preventing, controlling, or stopping the spread of Avian Influenza Virus (AIV) in the housing of a poultry flock in need thereof, comprising applying a composition to the floor of said housing in amounts effective to rapidly inactivate AIV, said composition comprising (i) salicylic acid; and (ii) one or more mineral salts.

Background Art

Avian Influenza Virus (AIV) and other avian viral diseases have always been and continue to be a major concern to the poultry industry. AIV infects specific tissues in many avian species, including tissues of the respiratory, digestive, and/or nervous system. While rarely fatal in wild birds, AIV is highly contagious and often fatal when transmitted to domestic poultry (Swayne, D. E. and Halvorson, D. A., "Influenza," in Saif, Y. M. et al., eds., *Diseases of Poultry*, 11th edition, Iowa State Press (2008); Capua, I. and Marangon, S., *Emerg Infect Dis* 12:1319-1324 (2006)).

AIVs in poultry have been categorized into two groups according to their ability to produce clinical signs and the severity of disease. Highly Pathogenic Avian Influenza (HPAI) viruses rapidly infect poultry and are often fatal, with a flock-fatality rate approaching 100%. Id. Low Pathogenic Avian Influenza (LPAI) viruses typically cause a much milder disease that can go undetected; however, the economic effect of LPAI lies in loss of production. Further, certain strains of LPAI viruses have the potential to mutate into HPAI viruses. The risk of LPAI and HPAI outbreaks in poultry flocks represent significant threats to the poultry industry, leading to the global culling of millions of birds, and the net loss of billions of dollars. These outbreaks are of concern, not only because of the degree of virulence observed in poultry resulting in severe economic consequences, but also due to the potential to transmit to the mammalian species, including humans. Thus, AIV is considered a zoonotic disease, i.e., a disease which primarily affects animals, but can be transmitted to humans.

Since 2003, highly pathogenic H5N1 strains of AIV have resulted in approximately 650 human cases, of which 384 were fatal (2013: World Health Organization (WHO) Influenza at the human animal interface). And surprisingly, human infection with the LPAI H7N9 AIV virus has been reported, with death occurring in nearly 33% of these approximately 150 cases (Centers for Disease Control and Prevention, 2014).

A major risk factor for AIV transmission to humans is direct contact and handling of domestic birds (Vong, S. et al., *Journal Infectious Diseases* 199:1744-1752 (2009); Dinh, P. N. et al., *Emerg Infectious Diseases* 12:1841-1847 (2006); Wang, M. et al., *Emerg Infectious Diseases* 12:1773-1775 (2006), so the majority of human cases have occurred when close proximity between humans and livestock leads to transmission. As the number of circulating viruses increases in domestic poultry, so do the risk for transmission to humans, and the potential for the virus to reassort into a form that is more transmissible among humans (Gatherer, D. et al., *Journal of Clinical Virology* 45:174-178 (2009). Therefore, with respect to reducing the risk to humans, AIV prevention in domestic poultry flocks is a large concern.

Current prophylactic methods for AIV in poultry are limited. Additionally, current vaccination strategies for poultry are limited as they do not confer complete immunity, are reliant on a healthy immune system, are susceptible to viral antigenic evolution, require individual handling of every bird in a large scale commercial poultry operation, have a limited shelf-life, and antibody protection following vaccination takes several weeks to acquire. Because of these challenges, AIV vaccination within the United States is rarely favored for prophylactic use in poultry. If an emergency vaccination program were adopted, it would offer little protection if administered during an outbreak, especially in densely populated poultry areas. Furthermore, growing evidence for the emergence of drug resistance AIV variants poses a risk for the use of drug therapies, such as amantadine, rimantadine, and oseltamivir. See, Capua, I. et al., *Avian Pathology* 22: 393-404 (2004); Escorcia, M. et al., *Virology Journal* 5:15 (2008). Further, some of the vaccines created for controlling HPAI outbreaks were precursors to new HPAI outbreaks.

In the absence of effective control, AIV outbreaks in poultry flocks can be devastating, and estimates of potential economic losses are enormous. This is specifically true when AIV epidemics hit areas that have a higher density of poultry farms. These areas become high-risk locations for outbreaks and often face considerable challenges to control AIV transmission, despite strict biosecurity measures and depopulation efforts. Once transmitted via respiratory secretions and feces, the incubation period for AIV may last as long as 10 days and the majority of infected poultry shed virus for 7 to 10 days, allowing the virus to circulate in a flock for a long period of time (Easterday, B. C. et al., in Calnek, B. W. et al., eds., *Diseases of Poultry*, 10th edition, Iowa State University Press (1997)). This potentially long shedding period increases the transmission risk to poultry flocks, especially within larger populations. Id. Developing rapid and effective anti-influenza technology is a critical step to effectively manage and control the spread of this disease in poultry to minimize financial losses and risks for transmission to other susceptible species, including humans.

Accordingly, there is a need in the art for a product and/or a method that can protect poultry flocks against different subtypes of Avian Influenza Virus, and also provide rapid inactivation of the virus should an outbreak occur.

BRIEF SUMMARY OF THE INVENTION

The methods described herein are suitable for rapidly preventing, controlling, or stopping the spread of Avian Influenza Virus (AIV) in the housing of a poultry flock in need thereof.

In one aspect, provided herein are methods for rapidly preventing, controlling, or stopping the spread of Avian Influenza Virus (AIV) in the housing of a poultry flock in need thereof comprising applying a composition, as described herein, to the floor of said housing in amounts effective to rapidly inactivate AIV, said composition comprising (i) salicylic acid; and (ii) one or more mineral salts, wherein said inactivation occurs within about ten to fifteen minutes after application of said composition, thereby preventing, controlling, or stopping the spread of AIV in said poultry flock housing.

In some embodiments, the floor of said poultry housing comprises bedding material.

In some embodiments, the AIV is a highly pathogenic strain. In some embodiments, the AIV is a low pathogenic strain.

In some embodiments, the AIV is H1N1, H2N2, H3N2, H4N2, H5N2, H5N3, H5N5, H5N8, H5N9, H7N2, or H9N2.

In some embodiments, the poultry flock comprises 1-1000 domestic birds. In some embodiments, the poultry flock comprises 1,001-1,000,000,000 domestic birds.

In some embodiments, the poultry flock housing is selected from the group consisting of barns, farms, hatcheries, chicken tractors, or any confined structure where one or more domestic birds reside.

In some embodiments, the composition is applied in access panels and nesting areas.

In some embodiments, the composition is applied up to about five square feet outside the housing of the poultry flock.

In some embodiments, the bedding material on the floor of the housing comprises wood shavings, paper pulp, recycled waste paper, cotton fiber, cotton seeds, cotton gin waste, newspaper, chopped cardboard, dried leaves, sawdust, hulls (e.g., peanut, cocoa, rice), hay, hemp, gypsum, sand, clay, straw, grass, reused poultry litter, compost, or any combination thereof.

In some embodiments, the poultry flocks comprise flocks of chickens, turkeys, quails, ducks, geese, pheasant, or guinea fowl. In some embodiments, the poultry flocks comprise flocks of chickens.

In some embodiments, the composition comprises salicylic acid in an amount ranging from about 0.0001 wt % to about 10 wt %; from about 0.001 wt % to about 10 wt %; from about 0.01 wt % to about 10 wt %; from about 0.1 wt % to about 10 wt %; from about 0.01 wt % to about 5 wt %; from about 1 wt % to about 10 wt %; from about 5 wt % to about 10 wt %; or from about 1 wt % to about 5 wt %. In some embodiments, the amount of salicylic acid in the composition ranges from about 1 wt % to about 10 wt %. In some embodiments, the amount of salicylic acid in the composition ranges from about 1 wt % to about 5 wt %. In some embodiments, the amount of salicylic acid in the composition is about 4 wt %.

In some embodiments, the one or more mineral salts in the composition are selected from the group consisting of $Na_2SO_4$, $K_2SO_4$, $CaSO_4$, $ZnSO_4$, $MgSO_4$, $Al_2SO_4$, $FeSO_4$, $Fe_2(SO_4)_3$, $Na_3PO_4$, $Na_2HPO_4$, $NaH_2PO_4$, $K_3PO_4$, $K_2HPO_4$, $KH_2PO_4$, $Ca_3(PO_4)_2$, $Ca_2H\ PO_4$, $CaH_2PO_4$, $Zn_3(PO_4)_2$, $Zn_2H\ PO_4$, $ZnH_2PO_4$, $Mg_3(PO_4)_2$, $Mg_2H\ PO_4$, $MgH_2PO_4$, $FePO4$, and $AlPO_4$, or combinations thereof.

In some embodiments, the one or more mineral salts comprise $Al_2SO_4$ and $CaSO_4$. In some embodiments, said one or more mineral salts comprise $Al_2SO_4$. In some embodiments, said one or more mineral salts comprise $CaSO_4$.

In some embodiments, the composition comprises $Al_2SO4$ in an amount ranging from about 0.1 wt % to about 30 wt %; from about 1 wt % to about 30 wt %; from about 1 wt % to about 20 wt %, from about 1 wt % to about 15 wt %; or from about 5 wt % to about 15 wt %.

In some embodiments, $Al_2SO_4$ is in an amount ranging from about 1 wt % to about 15 wt %. In some embodiments, $Al_2SO_4$ is in an amount ranging from about 5 wt % to about 15 wt %. In some embodiments, $Al_2SO_4$ is in an amount of about 8.5 wt %.

In some embodiments, the composition comprises $CaSO_4$ in an amount ranging from about 0.1 wt % to about 90 wt %; 0.1 wt % to about 50 wt %; from about 0.1 wt % to about 30 wt %; from about 1 wt % to about 90 wt %; from about 10 wt % to about 90 wt %; from about 20 wt % to about 90 wt %; from about 30 wt % to about 90 wt %; from about 40 wt % to about 90 wt %; from about 50 wt % to about 90 wt %; from about 60 wt % to about 90 wt %; from about 70 wt % to about 90 wt %; from about 80 wt % to about 90 wt %; or from about 85 wt % to about 90 wt %.

In some embodiments, the $CaSO_4$ is in an amount ranging from about 80 wt % to about 90 wt %.

In some embodiments, the $CaSO_4$ is in an amount ranging from about 85 wt % to about 90 wt %.

In some embodiments, the $CaSO_4$ is in an amount of about 87 wt %.

In some embodiments, the composition further comprises an odor abatement agent. In some embodiments, the odor abatement agent comprises at least one essential oil. In some embodiments, the at least one essential oil is selected from the group consisting of citrus oil, mint, fennel, geraniol, citronella, clove, lavender, *eucalyptus, pelargonium*, juniper, basil, and thyme, or combinations thereof. In some embodiments, the at least one essential oil is citronella. In some embodiments, the at least one essential oil is geraniol. In some embodiments, the at least one essential oil is citronella and geraniol.

In some embodiments, the citronella oil is in an amount ranging from about 0.005 wt % to about 0.05 wt %; from about 0.01 wt % to about 0.03 wt %; or in an amount of about 0.02 wt %; and said geraniol is in an amount ranging from about 0.01 wt % to about 0.1 wt %; from about 0.06 wt % to about 0.09 wt %; or about 0.08 wt %.

In some embodiments, the composition is applied to the floor of said poultry housing at a rate of about 1-3 pounds per 5-20 square feet of housing, or about 1-2 pounds per 10 square feet of housing. In some embodiments, the composition is applied to the floor of said poultry housing at a rate of about 1 pound per 10 square feet of housing. In some embodiments, the composition is applied to the floor of said poultry housing at a rate of about 2 pounds per 10 square feet of housing. In some embodiments, the composition is applied to the floor of said poultry housing at a rate of about ¼ to ½ pound per square feet of housing.

In some embodiments, the composition is applied to the housing as a spot treatment at a rate of about ¼ to ½ pound per square feet of housing. In some embodiments, the spot treatment is carried out on areas of the housing that are wet.

In some embodiments, the composition is applied to the bedding material at a rate of about 1-3 pounds per 5-20 square feet of housing. In some embodiments, the composition is applied to the bedding material at a rate of about 1-2 pounds per 10 square feet of housing. In some embodiments, the composition is applied to the bedding material at a rate of about 1 pound per 10 square feet of housing. In some embodiments, the composition is applied to the bedding material at a rate of about 2 pounds per 10 square feet of housing.

In some embodiments, the composition is in a solid form selected from the group consisting of a powder, a granule, a pastille, a pellet, a pulverized powder, and a tablet. In some embodiments, the composition is in the form of a powder.

DETAILED DESCRIPTION OF THE INVENTION

Definitions

To facilitate an understanding of the present invention, a number of terms and phrases are defined below.

As used herein, the term "avian influenza virus" or AIV refers to any Type A influenza virus that infects the avian species, although other non-avian species may be infected as well (i.e., AIV is a zoonotic disease). AIV is a member of the Orthomyxoviridae family, influenzavirus A genus.

AIVs are classified by a combination of two groups of proteins: the hemagglutinin or H proteins, of which there are 16 (i.e., H1-H16), and the neuraminidase or N proteins, of which there are 9 (i.e., N1-N9). Non-limiting examples of AIV subtypes include H1N1, H1N8, H2N2, H2N9, H3N2, H3N8, H4N2, H4N3, H4N6, H4N8, H5N1, H5N2, H5N3, H5N4, H5N5, H5N6, H5N8, H5N9, H6N1, H6N2, H6N5, H6N6, H6N8, H7N1, H7N2, H7N3, H7N7, H7N8, H7N9, H9N1, H9N2, H9N2, H9N6, H9N7, H9N8, H10N8, H11N6, H11N9, H12N5, H13N6, H14N4, and H15N9.

AIV strains are also divided into two groups based upon the ability of the virus to produce disease: low pathogenic (LP) and highly pathogenic (HP). The methods disclosed herein can be used to inactivate both LP and HP strains of avian influenza.

As used herein, the term "poultry," or alternatively, "domestic bird," encompasses chickens, turkeys, quails, ducks, geese, pheasant, and guinea fowl without limitation on age of the domestic bird. For example, chicks, ducklings, and gosslings are encompassed by the term poultry, in addition to mature birds.

As used herein, the term "chicken" encompasses chicks (baby chickens from hatching to about 6 weeks of age); broilers (6-8 weeks of age and about 2.5 lbs); fryers (6-8 weeks, weighing 2.5-3.5 pounds); stewing chickens (chickens (usually hens) that are over 10 months old and weigh 5-7 pounds); roosters (male chickens over 10 months old and weighing 6-8 pounds); capons (castrated male chickens weighing 6-8 pounds); and roasters (chickens less than 8 months old and weighing 3.5-5 pounds).

As used herein, the term "poultry flock" refers to a poultry production unit or operation comprising one or more domestic birds, as defined herein. The term poultry flock encompasses small-scale or "backyard" poultry flocks or large-scale poultry flocks such as commercial poultry production units. In some embodiments, the poultry flock comprises 1-1000 domestic birds, which as used herein, would be considered a small-scale poultry flock. In some embodiments, the poultry flock comprises 1,001-1,000,000,000 domestic birds, which as used herein, would be considered a large-scale poultry flock. The present invention, as described herein, is useful on all poultry flocks regardless of size or scale.

As used herein, the terms "house," "housing," "poultry housing," or "poultry flock housing" are used interchangeably, and refer to any contained structure where one or more domestic birds reside. In some embodiments, the poultry housing comprises and encompasses farms, barns, sheds, coops, hatcheries, and chicken tractors. In some embodiments, the poultry housing comprises and encompasses nesting areas within the poultry housing (also called breeder nests, nest areas, or nesting boxes). In some embodiments, the poultry housing comprises and encompasses access panels within the poultry housing. Those skilled in the poultry industry would be familiar with various types of poultry housing design. In some embodiments, the poultry housing comprises deep litter housing. In some embodiments, the poultry housing comprises slated housing. In some embodiments, the housing comprises a battery cage system. In some embodiments, the housing comprises a force-fed palmiped housing. While the term "in the poultry housing" or "in the house" generally applies to the contained structure where the domestic birds reside, the terms also encompass areas up to about five square feet from the housing where domestic birds with outside access may congregate.

As used herein, the term "poultry bedding" refers to the material or combination of materials that cover the floor of the poultry housing. In some embodiments, the poultry bedding material is comprised of wood shavings, paper pulp, recycled waste paper, cotton fiber, cotton seeds, cotton gin waste, newspaper, chopped cardboard, dried leaves, sawdust, hulls (e.g., peanut, cocoa, rice), hay, hemp, gypsum, sand, clay, straw, grass, reused poultry litter, compost, or a combination thereof. In some embodiments, the poultry bedding on the floor of the poultry housing comprises a depth of 2, 3, 4, or 5 inches of material.

As used herein, "compost" refers to bedding material that is composed of poultry manure blended with carbonaceous materials, such as wood shavings, paper pulp, recycled waste paper, cotton fiber, cotton seeds, cotton gin waste, newspaper, chopped cardboard, dried leaves, sawdust, hulls (e.g., peanut, cocoa, rice), hay, hemp, straw, and grass.

The poultry bedding, as defined herein, may be clean or dirty. "Clean poultry bedding" refers to poultry bedding that is applied to the floor of an empty (bird-free) house that is free of bedding material(s) on it, where the floor has been cleaned and disinfected prior to application of the bedding. "Dirty poultry bedding" refers to poultry bedding that is being applied to the floor of the housing that has bedding on it already. The birds may or may not be present in the housing during application of the dirty bedding. Composted poultry bedding refers to used poultry bedding that is stored and re-applied after a period of rest.

As used herein, the term "production cycle" refers to the length of time required to grow various types of domestic birds from the hatching of eggs.

In the commercial poultry industry, turkey growers traditionally follow a 16 week growth cycle after birds are received from the hatchery. For chicken growers, broilers typically follow a 6 week growth cycle or a 37 to 42 day growth cycle from the receipt of chicks to the transmission to processing plants. Broiler breeders produce eggs for hatcheries to incubate, then distribute chicks to broiler operations. Each flock typically begins egg production in 20 weeks, and produces eggs for up to 40 weeks.

An "effective amount" of the composition disclosed herein, is an amount sufficient to achieve the desired effect, i.e., to inactivate and/or reduce the spread of Avian Influenza Virus in the housing of a poultry flock. The effective amount of the composition is the amount: i) that can prevent AIV from infecting the poultry housing; (ii) that can reduce or eliminate the level of AIV in the poultry housing; (iii) that can inactivate a portion of AIV or 100% of AIV in the poultry housing, and/or (iv) that can reduce or stop the spread of AIV in the poultry housing.

As used herein, the term "inactivating" AIV refers to killing, stopping replication of, or spreading of AIV. In some embodiments, a portion of AIV in the poultry housing can be inactivated. In some embodiments, about 10%, about 20%, about 30%, about 40%, about 50%, about 60%, about 70%, about 75%, about 80%, about 85%, about 90%, about 95%, 96%, 97%, 98%, 99%, or 100% of AIV in the poultry housing is inactivated. In some embodiments, 100% of AIV in the poultry housing is inactivated.

As used herein, the term "rapidly" inactivates or inactivating AIV refers to a time frame ranging from a few minutes to a few hours, preferably within 10 to 30 minutes, more preferably within 10-15 minutes, most preferably within 10 minutes, from application of the composition to the bedding material on the floor of the poultry housing.

All numbers in this disclosure indicating amounts, ratios of materials, physical properties of materials, and/or use are to be understood as modified by the word "about," except as otherwise explicitly indicated. The term "about" when referring to a number or a numerical range means that the number or numerical range referred to is an approximation within experimental variability (or within statistical experimental error), and thus the number or numerical range can vary from, for example, between 1% and 15% of the stated number or numerical range.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

Methods of Rapidly Controlling the Spread of Avian Influenza Virus (AIV) in Poultry Flocks In one aspect, provided herein are methods of rapidly preventing, controlling, or stopping the spread of Avian Influenza Virus (AIV) in the housing of a poultry flock in need thereof, comprising: applying a composition to the floor of said housing in amounts effective to rapidly inactivate AIV, said composition comprising (i) salicylic acid; and (ii) one or more mineral salts, wherein said inactivation occurs within about ten to fifteen minutes after application of said composition, thereby preventing, controlling, or stopping the spread of AIV in said poultry flock housing.

Avian Influenza Virus (AIV) Strains

AIVs are classified by a combination of two groups of proteins: the hemagglutinin or H proteins, of which there are 16 (i.e., H1-H16), and neuraminidase or N proteins, of which there are 9 (i.e., N1-N9). Non-limiting examples of AIV subtypes (also known as strains) include: H1N1, H1N8, H2N2, H2N9, H3N2, H3N8, H4N2, H4N3, H4N6, H4N8, H5N1, H5N2, H5N3, H5N4, H5N5, H5N6, H5N8, H5N9, H6N1, H6N2, H6N5, H6N6, H6N8, H7N1, H7N2, H7N3, H7N7, H7N8, H7N9, H9N1, H9N2, H9N2, H9N6, H9N7, H9N8, H10N8, H11N6, H11N9, H12N5, H13N6, H14N4, and H15N9.

AIV strains are classified into two categories based upon the ability of the virus to cause disease and mortality—highly pathogenic avian influenza (HPAI) viruses and low pathogenic avian influenza (LPAI) viruses. The term low pathogenic or "low path" Avian Influenza (LPAI) virus refers to avian influenza virus that occurs naturally in wild birds and can spread to domestic birds. In most cases, infection of poultry with LPAI viruses causes no signs of infection or only minor symptoms (such as ruffled feathers and a drop in egg production). These strains of the disease pose little significant threat to human health. These strains are common in the U.S. and around the world. The term highly pathogenic or "high path" Avian Influenza (HPAI) virus refers to avian influenza virus that spreads rapidly and has a higher death rate in birds than LPAI. HPAI is often fatal in chickens and turkeys.

While the "highly pathogenic" and "low pathogenic" AIV terminology was originally based on lethality in experimentally inoculated chickens, molecular criteria were added to the definition in 1994 (See, USAHA, Report of the Committee of Transmissible Disease of Poultry and Other Avian Species: Criteria for determining that an AI virus isolation causing an outbreak must be considered for eradication, *Proc US Anim Heal Assoc.* 98:552 (1994)).

To foster international control of specific avian influenza viruses (as well as other threats to terrestrial animal health), the Office International des Epizooties ("OIE") in Paris, France (today known as the World Organisation for Animal Health, but maintaining the acronym OIE), publishes a Terrestrial Animal Health Code ("Terrestrial Code") that contributes to improving animal health and welfare and veterinary public health worldwide. The 2011 Terrestrial Code lists "notifiable" AIV as all HPAI (i.e., HPNAI) and all H5 and H7 LPAI (i.e., LPNAI). See, OIE, Terrestrial Animal Health Code, "Avian Influenza," chapter 10.4, Paris, France (2011). H5 and H7 LPAI viruses became LPNAI (i.e., "notifiable") in 2006 because these subtypes can mutate to the HP form when allowed to circulate in poultry populations.

The OIE Terrestrial Code (2017), Vol. II, chapter 10.4, entitled "Infection with Avian Influenza Viruses," now divides HPAI and LPAI AIV as follows:

1. HPAI viruses have an intravenous pathogenicity index (IVPI) in six-week-old chickens greater than 1.2 or, as an alternative, cause at least 75% mortality in four- to eight-week-old chickens infected intravenously. H5 and H7 viruses that do not have an IVPI of greater than 1.2 or cause less than 75% mortality in an intravenous lethality test should be sequenced to determine whether multiple basic amino acids are present at the cleavage site of the hemagglutinin molecule (HA0); if the amino acid motif is similar to that observed for other HPNAI isolates, the isolate being tested should be considered as HPAI viruses.

2. LPNAI viruses are all influenza A viruses of H5 and H7 subtypes that are not HPAI viruses. See, Id. and OIE: "Avian Influenza," in Manual of Diagnostic Tests and Vaccines for Terrestrial Animals, 15th ed., OIE, Paris, France, 302-309 (2006)).

In addition, the OIE code creates, by default, a third category of AIV—non-H5 and non-H7 LPAI viruses for which there is no formal requirement to report to OIE, unless they are causing a severe disease, but these viruses may be reportable to national and state/provincial authorities.

Being H5 or H7 subtypes are not predictors of HP; i.e., only a small percentage of H5 and H7 AIV have mutated to the HP phenotype. By contrast, all naturally occurring H1-H4, H6, and H8-H16 viruses have been of low virulence (i.e., LP) for chickens when given by the natural route of challenge in experimental settings.

As used herein, the terms "high pathogenicity" and "low pathogenicity" AIV encompass any of the above discussed criteria for determining pathogenicity that will be known to those skilled in the art of AIV virology. Further, the methods disclosed herein are applicable to all AIV subtypes and strains regardless of pathogenicity.

In some embodiments, the avian influenza virus has low pathogenicity.

In some embodiments, the avian influenza virus is highly pathogenic.

In some embodiments, the AIV strains that can be rapidly inactivated by the composition applied in the described methods is selected from the group consisting of H1N1, H2N2, H3N2, H4N2, H5N2, H5N3, H5N5, H5N8, H5N9, H7N2, and H9N2.

Both HPAI and LPAI viruses can spread rapidly through poultry flocks. Thus, poultry flocks generally are considered "in need thereof" of AIV prevention, and/or control, and/or stopping the spread of AIV.

The compositions used in the methods disclosed herein can be used to rapidly inactivate all strains of AIV, i.e., both highly pathogenic and low pathogenic AIV strains, as well as AIV strains that have mutated from one form to another (i.e., low pathogenic to highly pathogenic), or are of mixed origin (e.g., containing a highly pathogenic H5 part of the virus together with an N part of the viruses from a low pathogenic AIV strain).

Components of the Composition Used in the Claimed Methods

Unless stated otherwise, the components listed below (i.e., salicylic acid, mineral salts, and additional ingredients) can be used in combination.

i) Salicylic Acid

The composition used in the methods described herein comprises salicylic acid or a salt thereof. Suitable salts include, but are not limited to, those formed by reacting salicylic acid with an organic base (such as an amine compound) or an inorganic base (such as NaOH, KOH, $Ca(OH)_2$, $Ba(OH)_2$). In some embodiments, the composition used in the methods described herein comprises salicylic acid.

In some embodiments, the salicylic acid or salt thereof in the composition is in an amount ranging from about 0.0001 wt % to about 10 wt %; from about 0.001 wt % to about 10 wt %; from about 0.01 wt % to about 10 wt %; from about 0.1 wt % to about 10 wt %; from about 0.01 wt % to about 5 wt %; from about 1 wt % to about 10 wt %; from about 5 wt % to about 10 wt %; or from about 1 wt % to about 5 wt %. In a preferred embodiment, the salicylic acid or salt thereof in the composition is in an amount no more than about 5 wt %, for example, ranging from about 1 wt % to about 5 wt %. In a particularly preferred embodiment, the salicylic acid or salt thereof in the composition is in an amount of about 4 wt %.

ii) Mineral Salts

In addition to salicylic acid or a salt thereof, the composition used in the methods described herein comprises one or more mineral salts. In some embodiments, the one or more mineral salts are selected from the group consisting of $Na_2SO_4$, $K_2SO_4$, $CaSO_4$, $ZnSO_4$, $MgSO_4$, $Al_2SO_4$, $FeSO_4$, $Fe_2(SO_4)_3$, $Na_3PO_4$, $Na_2HPO_4$, $NaH_2PO_4$, $K_3PO_4$, $K_2PO_4$, $KH_2PO_4$, $Ca_3(PO_4)_2$, $Ca_2HPO_4$, $CaH_2PO_4$, $Zn_3(PO_4)_2$, $Zn_2HPO_4$, $ZnH_2PO_4$, $Mg_3(PO_4)_2$, $Mg_2HPO_4$, $MgH_2PO_4$, $FePO_4$, and $AlPO_4$.

In some embodiments, the composition used in the method described herein contains aluminum sulfate ($Al_2SO_4$) or calcium sulfate ($CaSO_4$), or a combination of aluminum sulfate ($Al_2SO_4$) and calcium sulfate ($CaSO_4$). In a preferred embodiment, the composition used in the method described herein comprises aluminum sulfate ($Al_2SO_4$) and calcium sulfate ($CaSO_4$).

In some embodiments, the aluminum sulfate in the composition is in an amount ranging from about 0.1 wt % to about 30 wt %; from about 1 wt % to about 30 wt %; from about 1 wt % to about 20 wt %, from about 1 wt % to about 15 wt %; or from about 5 wt % to about 15 wt %. In a preferred embodiment, the aluminum sulfate in the composition is in an amount ranging from about 5 wt % to about 15 wt %. In a particularly preferred embodiment, the aluminum sulfate in the composition is in an amount of about 8.5 wt %.

In some embodiments, the calcium sulfate in the composition is in an amount ranging from about 0.1 wt % to about 90 wt %; 0.1 wt % to about 50 wt %; from about 0.1 wt % to about 30 wt %; from about 1 wt % to about 90 wt %; from about 10 wt % to about 90 wt %; from about 20 wt % to about 90 wt %; from about 30 wt % to about 90 wt %; from about 40 wt % to about 90 wt %; from about 50 wt % to about 90 wt %; from about 60 wt % to about 90 wt %; from about 70 wt % to about 90 wt %; from about 80 wt % to about 90 wt %; or from about 85 wt % to about 90 wt %. In a preferred embodiment, the calcium sulfate in the composition is in an amount ranging from about 85 wt % to about 90 wt %. In a particularly preferred embodiment, the calcium sulfate in the composition is in an amount of about 87 wt %.

iii) Additional Ingredients

In some embodiments, the composition used in the methods described herein may further comprise one or more odor abatement agents, including but not limited to, essential oils, such as, e.g., citrus oil (e.g., bergamot, grapefruit, lemon, lime, orange, and tangerine), mint, fennel, geraniol, citronella, clove, lavender, *eucalyptus, pelargonium*, juniper, basil, and thyme. Those skilled in the art would be aware of other essential oils that can be included in the composition used in the methods described herein. See, e.g., Sell, C., Chapter 5: "The Chemistry of Essential Oils," in Can Baser, K. H. and Buchbauer, G. (eds.), *Handbook of Essential Oils: science, technology, and applications*, pp. 121-150, CRC Press, Boca Raton, Fla. (2010). In some embodiments, the odor abatement agent is citronella oil. In some embodiments, the odor abatement agent is geraniol. In some embodiments, the odor abatement agents are geraniol and citronella oil.

In one embodiment, the geraniol in the composition is in an amount ranging from about 0.01 wt % to about 0.1 wt %. In a preferred embodiment, the geraniol in the composition is in an amount ranging from about 0.06 wt % to about 0.09 wt %. In a particularly preferred embodiment, the geraniol in the composition is in an amount of about 0.08 wt %.

In one embodiment, the citronella oil in the composition is in an amount ranging from about 0.005 wt % to about 0.05 wt %. In a preferred embodiment, the citronella oil in the composition is in an amount ranging from about 0.01 wt % to about 0.03 wt %. In a particularly preferred embodiment, the citronella oil in the composition is in an amount of about 0.02 wt %.

Supplementary active compounds can also be incorporated into the compositions used in the methods of the present invention. For example, the salicylic acid and mineral salts can be coformulated with one or more additional agents, such as activated carbon or silica gel, or claylike ingredients, including calcium silicate, aluminum silicate, magnesium aluminum silicate, sodium magnesium silicate, zirconium silicate, fuller's earth, kaolin, montmorillonite, pyrophyllite, and zeolite.

In some embodiments, the composition used in the methods described herein contains one or more inactive ingredients, such as absorbents, fillers, or carriers, for example, clay, sand, chlorite salt, carbonate salt, gypsum or limestone.

iv) Forms of the Composition

The composition used in the methods described herein can be in any solid form, such as a powder, a granule, a pastille, a pellet, a pulverized powder, or a tablet. In a preferred embodiment, the composition is in a powder form.

An exemplary powdered composition suitable for use in the methods described herein is available from TIMAC AGRO USA (153 Angstadt Lane, Reading, Pa.) under the commercial product name Shield Plus.

v) Application Rate of the Composition

As described below, the application rate of the composition will depend on various factors, including, for example, the occupancy or density of birds in the poultry housing, the type of poultry housing, as well as the condition of the bedding on the floor of the poultry housing prior to application of the composition (i.e., clean, dirty, wet, dry).

Empty Poultry House (No Birds Present).

In some embodiments, the composition, as described herein, is applied to the bedding material on the floor of an empty poultry house at a rate of about 1-3 pounds per 5-20 square feet of housing.

In some embodiments, the composition, as described herein, is applied to the bedding material on the floor of an empty poultry house at a rate of about 1-2 pounds per about 10 square feet of housing. In some embodiments, the composition, as described herein, is applied to the bedding material on the floor of an empty poultry house at a rate of about 1 pound per about 10 square feet of housing. In some embodiments, the composition, as described herein, is applied to the bedding material on the floor of an empty poultry house at a rate of about 2 pounds per about 10 square feet of housing. In some embodiments, the composition, as described herein, is applied to clean bedding material on the floor of an empty poultry house at a rate of about 1 pound per 10 square feet of housing.

In some embodiments, the composition should be spread evenly on the bedding material on the floor of the poultry housing using a standard spreader or a drop lime spreader to ensure accurate coverage.

In some embodiments, the composition is applied on dirty bedding material in an empty poultry house at a rate of about 2 pounds per 10 square feet of housing.

In some embodiments, the composition is applied to bedding material in a slated empty poultry house at a rate of about 2 pounds per 10 square feet.

In some embodiments, the composition is applied to bedding material comprising compost in an empty poultry house at a rate of about 2 pounds per 10 square feet.

In some embodiments, the composition, as described herein, is applied to the floor of the poultry housing that does not have any bedding material on it. In some embodiments, the composition is applied to the floor at a rate of about 1-3 pounds per 5-20 square feet of housing. In some embodiments, the composition, as described herein, is applied to the floor of an empty poultry house at a rate of about 1-2 pounds per about 10 square feet of housing. In some embodiments, the composition, as described herein, is applied to floor of an empty poultry house at a rate of about 1 pound per about 10 square feet of housing. In some embodiments, the composition, as described herein, is applied to the floor of an empty poultry house at a rate of about 2 pounds per about 10 square feet of housing.

The application can be as frequent as needed. For example, the composition can be applied multiple times a day, daily, weekly, or monthly. In some embodiments, the composition is applied about every day, about every 2 days, about every 3 days, about every 4 days, about every 5 days, about every 6 days, about every 7 days, or about twice every week, about once every 1 to 9 weeks, about once every week, about once every 2 weeks, about once every 3 weeks, about once every 4 weeks, about once every 5 weeks, about once every 6 weeks, about once every 7 weeks, about once every 8 weeks, or about once every 9 weeks.

In some embodiments, the composition, as described herein, is further applied to the manure area, walk alleys, and barn ends of confinement-style barns at a rate of about 2 pounds per 10 square feet. In some embodiments, the composition can be applied 2-4 times during the production cycle. There is no upper limit on the application rate of the composition described herein, except what may be determined to be an economic or financial limitation.

Occupied House (Birds Present).

In some embodiments, when birds are present in the house, "spot treatment" of the disclosed composition can be applied. In some embodiments, spot treatment of the composition can be applied to feed areas, under water lines, wet areas, and corners of the house. In some embodiments, if the birds have access to outside the house, spot treatment can also be applied inside the access panels and nesting areas. In some embodiments, spot treatments can be done every one to two weeks at a rate of ¼ to ½ pound per square foot of housing.

Those skilled in the art will appreciate that the rate and frequency of application of the composition described herein can be modified (decreased or increased) based upon a variety of factors, such as, e.g., the number of birds in the housing, the health of the birds in the housing, the condition of the poultry bedding, the time interval between application of the composition, the timing of the production cycle, the knowledge of an AIV outbreak in nearby poultry flocks, etc. In addition, the need to adjust (such as increase or decrease) application rate and/or application frequency can be based on poultry health and environmental conditions. For example, application rate and/or application frequency should be increased when AIV is present in the geographical location of a poultry flock that is in need of rapidly preventing, controlling, or stopping the spread of AIV. There is no upper limit on the application rate of the composition described herein, except what may be determined to be an economic or financial limitation.

EXAMPLES

The following illustrative examples are representative of embodiments of the methods described herein and are not meant to be limiting in any way.

Example 1: Inactivation Studies of Shield Plus on AIV Subtypes H1 Through 119

Materials:

In this inactivation study, the antiviral effect of Shield Plus (Timac Agro, USA) was tested on low pathogenicity AIV subtypes H1 through H9 (i.e., H1N1, H2N2, H3N2, H4N2, H5N2, H5N3, H5N5, H5N8, H5N9, H7N2, and H9N2), at varying concentrations of Shield Plus and at varying incubation times. AIV subtypes H1 through H9 were obtained from the Wiley Avian Virology Laboratory of Penn State University. Embryonating chicken eggs (ECE), 9-11 days old, were used to test viral inactivation.

Methods:

Dilution of the AIV Test Virus:

Each AIV test virus was diluted with sterile $dH_2O$ at 1:100; for each test run: 0.4 ml virus (in allantoic fluid (AF), undiluted)+40 ml $dH_2O$ in a 50 ml centrifuge tube.

Making Different Concentrations of the Shield Plus Powder:

The Shield Plus powder, in the amounts of 1.0 g, 0.5 g, 0.2 g, and 0.1 g, was placed into 15 ml centrifuge tubes with 10 ml distilled water, in order to obtain 10%, 5%, 2%, and 1% concentrations of Shield Plus, respectively.

Each AIV test virus was tested for inactivation at all four concentrations of Shield Plus.

Adding Virus to the Shield Plus:

Incubation times began when, the test viruses (at 10 ml virus) were added to the 15 ml centrifuge tubes containing the four concentrations of Shield Plus, as follows:

1:10 Shield Plus dilution (10% Shield Plus)=1.0 g Shield Plus+10 ml virus (in $dH_2O$ at 1:100);

1:20 Shield Plus dilution (5% Shield Plus)=0.5 g Shield Plus+10 ml virus (in $dH_2O$ at 1:100);

1:50 Shield Plus dilution (2% Shield Plus)=0.2 g Shield Plus+10 ml virus (in $dH_2O$ at 1:100); and 1:100 Shield Plus dilution (1% Shield Plus)=0.1 g Shield Plus+10 ml virus (in $dH_2O$ at 1:100);

The Shield Plus-virus mixtures were mixed in a shaker and incubated at room temperature (RT) for 10-15 minutes or 30 minutes.

Inoculating the Embryonating Chicken Eggs (ECE):

Each preparation (i.e., mixture of Shield Plus+virus) was inoculated in five (5) embryonating chicken eggs (ECE) after each incubation time (10-15 minutes or 30 minutes) for each concentration of Shield Plus. The inoculated ECE were incubated at 37° C. in an egg incubator for 3 days, then allantoic fluid (AF) samples were harvested for the hemagglutination-inhibition (HI or HAI) test in order to detect the presence of AIV. HI negative results indicated no growth of the virus (i.e., successful virus inactivation). HI positive results indicated the presence of the virus (i.e., the virus was not inactivated). See Thayer, S. G., and Beard, C. W., "Chapter 46—Serologic Procedures," in Swayne, D. E. et al., eds., A Laboratory Manual for the Isolation and Identification of Avian Pathogens, International Book Distributing Co., India (2006).

Results:

As shown in Table 1, Shield Plus effectively inactivated the eleven tested AIV subtypes H1N1, H2N2, H3N2, H4N2, H5N2, H5N3, H5N5, H5N8, H5N9, H7N2, and H9N2 100% of the time, compared to 0% for positive controls, at concentrations of 10%, 5%, and 2% Shield Plus, and at incubation times of 10-15 minutes and 30 minutes. One percent concentrations of Shield Plus partially inactivated (10-50%) the four AIV strains tested (H1N1, H3N2, H5N2, H7N2) at up to 30 minutes of reaction time.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All publications, patents, patent applications, internet sites, and accession numbers/database sequences cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. A method of rapidly inactivating Avian Influenza Virus (AIV) in the housing of a poultry flock in need thereof, comprising:
    applying a powdered composition to the floor of said housing in amounts effective to rapidly inactivate AIV, said floor of said poultry housing comprising bedding

TABLE 1

Results of Shield Plus for Inactivation Test of AIV Subtypes H1 through H9

| Avian Influenza Virus (AIV) subtypes | Concentration of Shield Plus (%) in AIV inactivation test | | | | | | | | Positive Control |
|---|---|---|---|---|---|---|---|---|---|
| | 10% | | 5% | | 2% | | 1% | | 0% |
| | 10-15 min | 30 min | 10-15 min | 30 min | 10-15 min | 30 min | 10-15 min | 30 min | 30 min |
| H1N1 | 100% | 100% | 100% | 100% | 100% | 100% | 10-20% | 25% | 0% |
| H2N2 | 100% | 100% | 100% | 100% | 100% | 100% | ND | ND | 0% |
| H3N2 | 100% | 100% | 100% | 100% | 100% | 100% | 20-30% | 25% | 0% |
| H4N2 | 100% | 100% | 100% | 100% | 100% | 100% | ND | ND | 0% |
| H5N2 | 100% | 100% | 100% | 100% | 100% | 100% | 40-50% | 50% | 0% |
| H5N3 | 100% | 100% | 100% | 100% | 100% | 100% | ND | ND | 0% |
| H5N5 | 100% | 100% | 100% | 100% | 100% | 100% | ND | ND | 0% |
| H5N8 | 100% | 100% | 100% | 100% | 100% | 100% | ND | ND | 0% |
| H5N9 | 100% | 100% | 100% | 100% | 100% | 100% | ND | ND | 0% |
| H7N2 | 100% | 100% | 100% | 100% | 100% | 100% | 0% | 10% | 0% |
| H9N2 | 100% | 100% | 100% | 100% | 100% | 100% | ND | ND | 0% |

Notes:
100% = 100% virus inactivation results;
0% = the virus was not inactivated;
ND = Not Done material, said composition comprising (i) salicylic acid in an amount ranging from about 1 wt % to about 5 wt %; and (ii) aluminum sulfate in an amount ranging from about 5 wt % to about 15 wt % and calcium sulfate in an amount ranging from about 80 wt % to about 90 wt %, wherein said inactivation of AIV occurs within about ten to fifteen minutes after application of said composition, and wherein said AIV is a low pathogenic strain.

2. The method of claim 1, wherein said AIV is H1N1, H2N2, H3N2, H4N2, H5N2, H5N3, H5N5, H5N8, H5N9, H7N2, or H9N2.

3. The method of claim 1, wherein said poultry flock housing is selected from the group consisting of barns, farms, hatcheries, chicken tractors, or any confined structure where one or more domestic birds reside.

4. The method of claim 1, wherein said bedding material comprises wood shavings, paper pulp, recycled waste paper, cotton fiber, cotton seeds, cotton gin waste, newspaper, chopped cardboard, dried leaves, sawdust, hulls (e.g., peanut, cocoa, rice), hay, hemp, gypsum, sand, clay, straw, grass, reused poultry litter, compost, or any combination thereof.

5. The method of claim 1, wherein said poultry flocks comprise flocks of chickens, turkeys, quails, ducks, geese, pheasant, or guinea fowl.

6. The method of claim 5, wherein said poultry flocks comprise flocks of chickens.

7. The method of claim 1, wherein the amount of salicylic acid in the composition is about 4 wt %.

8. The method of claim 1, further comprising one or more mineral salts selected from the group consisting of $Na_2SO_4$, $K_2SO_4$, $ZnSO_4$, $MgSO_4$, $FeSO_4$, $Fe_2(SO_4)_3$, $Na_3PO_4$, $Na_2HPO_4$, $NaH_2PO_4$, $K_3PO_4$, $K_2HPO_4$, $KH_2PO_4$, $Ca_3(PO_4)_2$, $Ca_2HPO_4$, $CaH_2PO_4$, $Zn_3(PO_4)_2$, $Zn_2HPO_4$, $ZnH_2PO_4$, $Mg_3(PO_4)_2$, $Mg_2HPO_4$, $MgH_2PO_4$, $FePO4$, and $AlPO_4$, or combinations thereof.

9. The method of claim 1, wherein said composition comprises aluminum sulfate in an amount of about 8.5 wt %.

10. The method of claim 1, wherein said composition comprises calcium sulfate in an amount of about 87 wt %.

11. The method of claim 8, wherein said composition further comprises an odor abatement agent comprising at least one essential oil.

12. The method of claim 11, wherein said at least one essential oil is selected from the group consisting of citrus oil, mint, fennel, geraniol, citronella, clove, lavender, eucalyptus, pelargonium, juniper, basil, and thyme, or combinations thereof.

13. The method of claim 12, wherein said at least one essential oil is citronella.

14. The method of claim 12, wherein said citronella oil is in an amount ranging from about 0.005 wt % to about 0.05 wt %; from about 0.01 wt % to about 0.03 wt %; or in an amount of about 0.02 wt %; and said geraniol is in an amount ranging from about 0.01 wt % to about 0.1 wt %; from about 0.06 wt % to about 0.09 wt %; or about 0.08 wt %.

15. The method of claim 1, wherein said composition is applied to the floor of said housing at a rate of about 1-3 pounds per 5-20 square feet of housing.

16. The method of claim 15, wherein said composition is applied to the floor of said housing at a rate of about 1-2 pounds per 10 square feet of housing.

17. The method of claim 1, wherein said composition is applied to said housing as a spot treatment at a rate of about ¼ to ½ pound per square feet of housing.

18. The method of claim 1, wherein said composition is applied to the bedding material at a rate of about 1-3 pounds per 5-20 square feet of housing.

19. The method of claim 18, wherein said composition is applied to the bedding material at a rate of about 1-2 pounds per 10 square feet of housing.

* * * * *